US009750517B2

(12) United States Patent
Agrawal

(10) Patent No.: US 9,750,517 B2
(45) Date of Patent: Sep. 5, 2017

(54) METHOD OF ASPIRATING A THROMBUS ACCUMULATION BETWEEN A VENOUS VALVE AND A VEIN WALL

(71) Applicant: COOK MEDICAL TECHNOLOGIES LLC, Bloomington, IN (US)

(72) Inventor: Sony Agrawal, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1076 days.

(21) Appl. No.: 13/905,356

(22) Filed: May 30, 2013

(65) Prior Publication Data

US 2014/0358159 A1  Dec. 4, 2014

Related U.S. Application Data

(62) Division of application No. 13/093,352, filed on Apr. 25, 2011, now abandoned.

(51) Int. Cl.
*A61B 17/22* (2006.01)
*A61B 17/00* (2006.01)

(52) U.S. Cl.
CPC ........ *A61B 17/22* (2013.01); *A61B 2017/003* (2013.01); *A61B 2017/22054* (2013.01); *A61B 2017/22067* (2013.01); *A61B 2017/22072* (2013.01); *A61B 2017/22079* (2013.01); *A61B 2017/22082* (2013.01); *A61B 2017/22094* (2013.01); *A61B 2017/22098* (2013.01); *A61B 2217/007* (2013.01)

(58) Field of Classification Search
CPC .............. A61B 17/22; A61B 17/22079; A61B 17/22098; A61B 17/3207; A61B 2217/005
See application file for complete search history.

(56) References Cited

U.S. PATENT DOCUMENTS

| | | |
|---|---|---|
| 4,309,994 A | 1/1982 | Grunwald |
| 4,925,452 A | 5/1990 | Melinyshyn et al. |
| 5,419,774 A | 5/1995 | Willard et al. |
| 5,904,648 A | 5/1999 | Arndt et al. |
| 6,022,336 A | 2/2000 | Zadno-Azizi et al. |
| 6,398,773 B1 * | 6/2002 | Bagaoisan ............ A61B 17/22 604/101.04 |
| 6,569,148 B2 | 5/2003 | Bagaoisan et al. |
| 6,929,633 B2 | 8/2005 | Evans et al. |
| 6,979,290 B2 | 12/2005 | Mourlas et al. |
| 7,402,151 B2 | 7/2008 | Rosenman et al. |
| 7,578,295 B2 | 8/2009 | Kurrus |
| 7,608,056 B2 | 10/2009 | Kennedy, II |
| 7,713,260 B2 | 5/2010 | Lessard et al. |
| 8,241,241 B2 | 8/2012 | Evans et al. |
| 8,267,953 B2 | 9/2012 | Gurm |
| 9,332,998 B2 * | 5/2016 | Ray ................. A61B 17/22012 |

(Continued)

*Primary Examiner* — Diane Yabut
(74) *Attorney, Agent, or Firm* — Brinks Gilson & Lione

(57) ABSTRACT

A method of removing thrombus accumulation from a space between a body valve and a wall of a body vessel is described herein. The method can include an occlusion catheter with a first occlusion member positioned on the second side of the vessel. An aspiration catheter is introduced through the vessel and the valve. The aspiration catheter can have a nozzle with a bent configuration to position the end opening proximate to the thrombus accumulation.

20 Claims, 5 Drawing Sheets

(56) References Cited

U.S. PATENT DOCUMENTS

| | | |
|---|---|---|
| 2002/0029031 A1 | 3/2002 | Bagaoisan et al. |
| 2004/0049225 A1* | 3/2004 | Denison ............... A61B 17/221 |
| | | 606/200 |
| 2005/0228402 A1 | 10/2005 | Hofmann |
| 2006/0149350 A1* | 7/2006 | Patel ....................... A61F 2/954 |
| | | 623/1.11 |
| 2006/0200191 A1 | 9/2006 | Zadno-Aziz et al. |
| 2006/0293647 A1 | 12/2006 | McRae et al. |
| 2008/0243153 A1* | 10/2008 | Nguyen ........... A61B 17/32037 |
| | | 606/159 |
| 2008/0275393 A1 | 11/2008 | Bonnette et al. |
| 2010/0036314 A1 | 2/2010 | Burton et al. |
| 2010/0063537 A1* | 3/2010 | Ren ......................... A61F 2/013 |
| | | 606/200 |
| 2010/0087844 A1 | 4/2010 | Fischer, Jr. |
| 2010/0211087 A1 | 8/2010 | Osborne |

\* cited by examiner

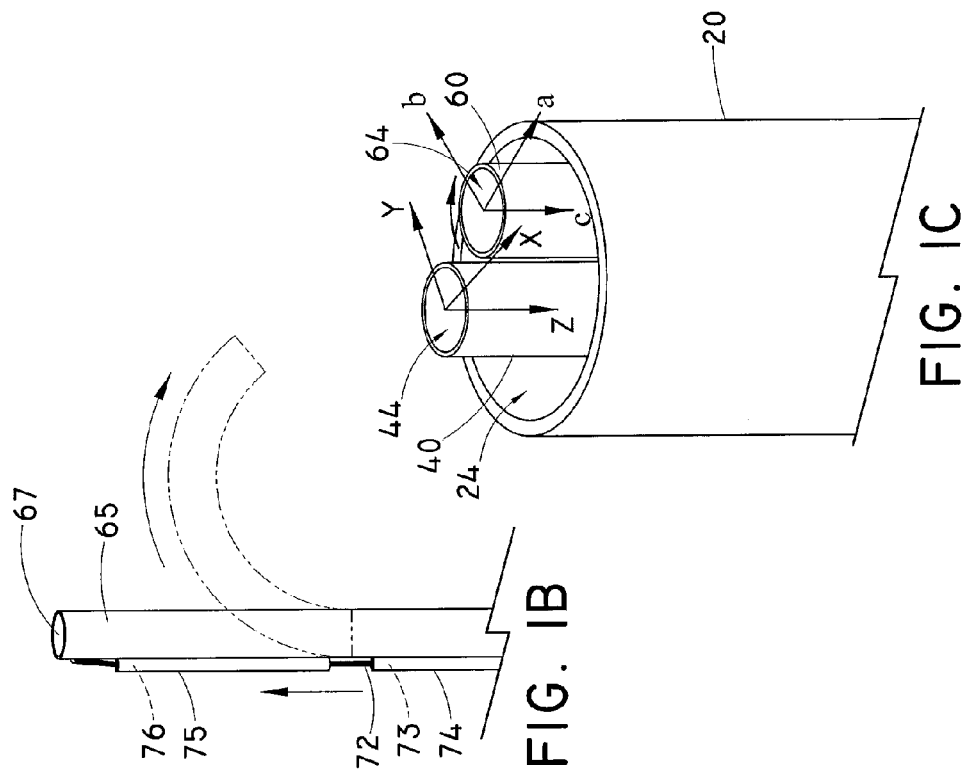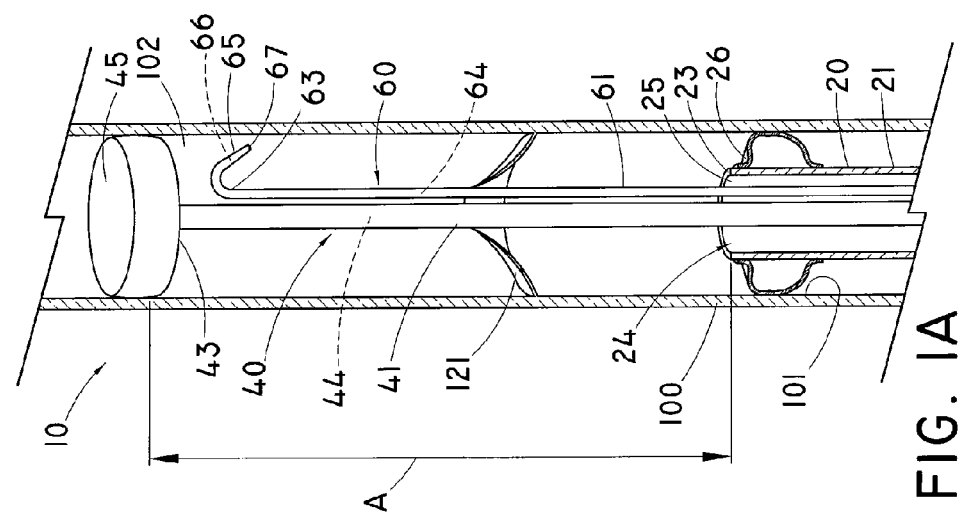

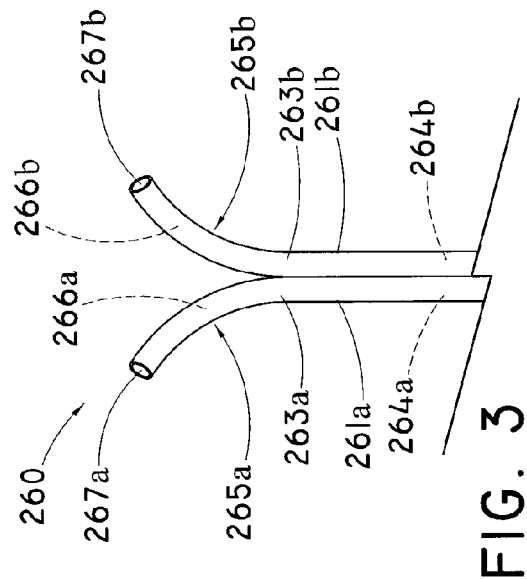
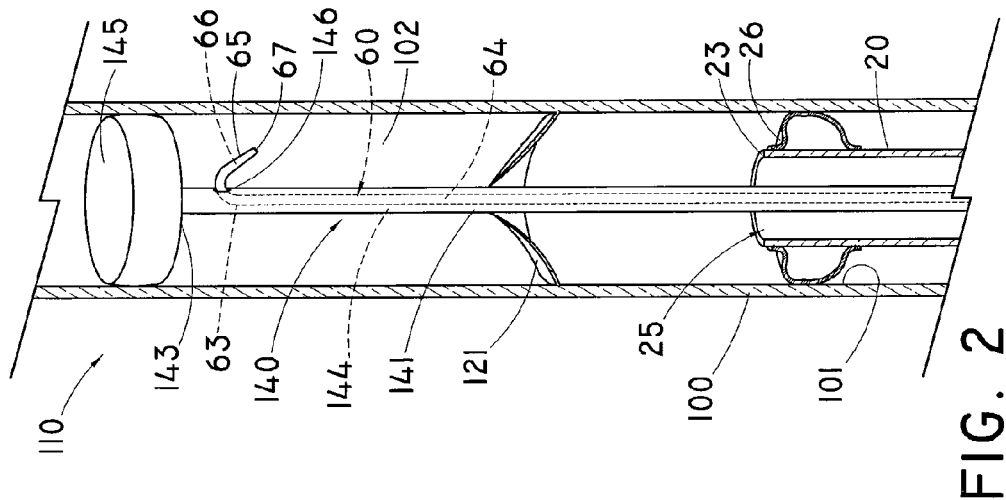

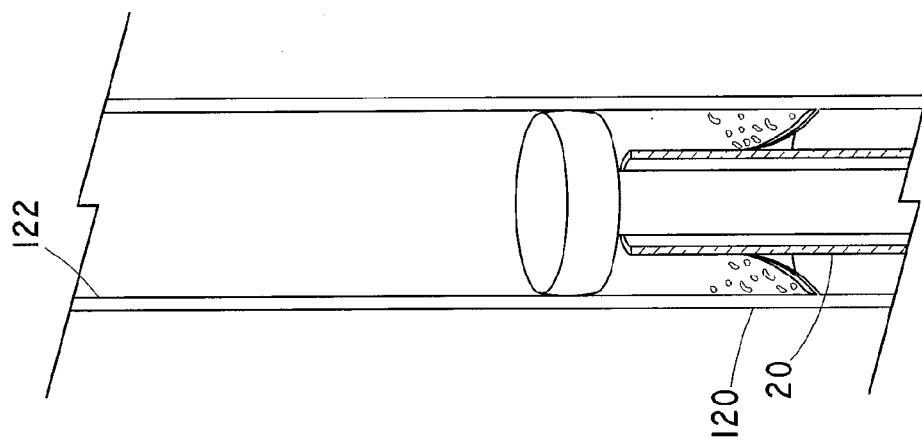
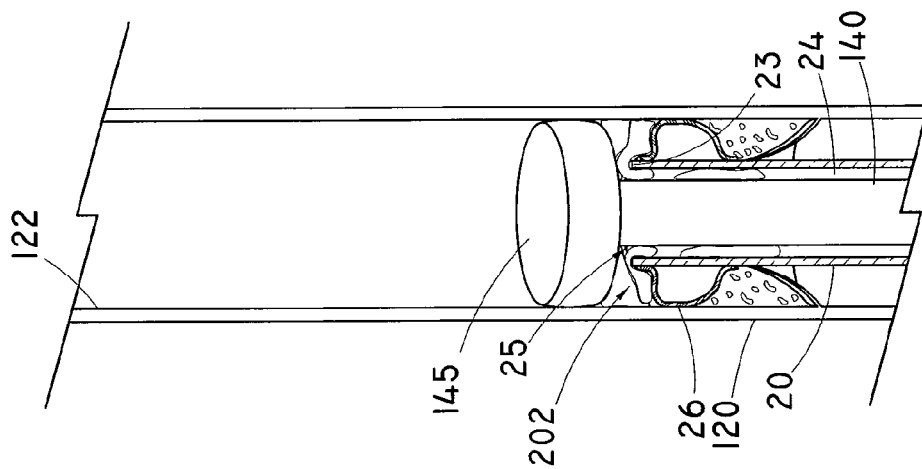
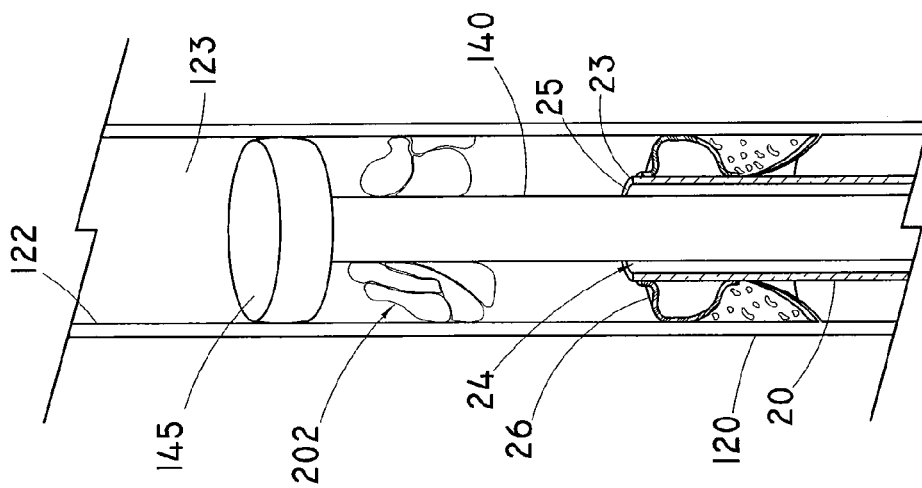

METHOD OF ASPIRATING A THROMBUS ACCUMULATION BETWEEN A VENOUS VALVE AND A VEIN WALL

This application claims the benefit under 35 U.S.C. §121 as a division of U.S. patent application Ser. No. 13/093,352, filed Apr. 25, 2011, which is hereby incorporated by reference herein.

BACKGROUND

The present disclosure relates generally to medical devices. More particularly, it relates to thrombectomy devices for removing thrombus deposits from a space between a body valve and a wall of a body vessel.

Vascular disease affects a large proportion of individuals each year. One indication of the existence of this disease is the development of a blood clot in the vascular system, which if left untreated may result in deep vein thrombosis, embolisms, or ischemic. Thrombi within the vasculature can form as a result of a variety of causes, such as trauma, disease, surgery, stagnant blood, and foreign devices in the vasculature. These clots are usually comprised of an aggregated mixture of thrombus and fibrin. Typically, a thrombus present in an arterial blood vessel tends to migrate in the direction of flow from a large diameter artery to smaller diameter arteries. The thrombus continues to flow with the blood until it becomes lodged against the vessel wall and is unable to advance. In some instances, the thrombus partially or completely blocks blood flow through the artery thereby preventing blood from reaching the tissue disposed downstream of the thrombus. Denying blood flow for an extended period of time can result in damage or death of the tissue beyond the blockage. The result can be loss of toes or fingers, or even an entire limb in more severe circumstances. Moreover, thrombi in the venous system can migrate to the lungs and become a pulmonary embolus, which is usually fatal. In other instances, thrombi can migrate into the cerebral circulation and cause stroke and death.

Various known techniques for the removal of blood clots include both chemical and mechanical treatment. Chemical treatment typically involves the injection of lysine agents into the vessel near the blood clot to chemically attack, dissolve, and disperse the occlusion. In this technique, the lysine agent is brought into the proximate vicinity of the blood clot by injection through a cannula or other lumen.

The mechanical treatment of a blood clot typically involves the use of catheters having a rotary cutting head or other form of a rotor-stator homogenizing head. Examples of such rotary devices include rotating burr devices, devices with a rotating helical coil wire within a catheter, and recanalization catheters. Other mechanical devices utilize a balloon that is inflated in a vessel and then withdrawn to pull a clot into a conventional sheath. The sheath may then be withdrawn from the patient to remove the captured clot or the clot may be aspirated into the sheath and removed from the patient. Still other mechanical devices utilize a sharp point to pierce the occlusion to form a hole therethrough. In each of these cases, although the occlusion is reduced in size or a passageway is created, the residual thrombus/fibrin material resulting from the treatment remains within the vessel.

Although these treatment devices and methods may be adequate to remove the majority of a clot, they do not effectively remove the residual material formed during fragmentation of a blood clot or the accumulation of thrombus material disposed in the space between a body valve and a body vessel wall. Removal of such residual material and/or accumulated material is medically desirable. It is further necessary to ensure that this residual material and/or accumulated material does not migrate away from the site of the treatment to other parts of the vessel. Such migration could lead to serious complications, such as embolism, stroke, or heart attack.

Thus, what is needed is a device for removing the thrombus material from a space between a body valve and a body vessel wall. It would be desirable if such device is easy for a physician to use and compatible with existing thrombectomy methods.

SUMMARY

Accordingly, a thrombectomy system is provided herein to address at least some of the shortcomings of the prior art. The system can be used for removing a thrombus accumulation from a space between a body valve and the wall of a body vessel. In one example, the system can include a thrombectomy catheter having a proximal end, a distal end, and a thrombectomy lumen extending longitudinally therein. A first occlusion member can be disposed around an outer circumference of the distal end of the thrombectomy catheter. The first occlusion member can be moveable between a non-expanded configuration and an expanded configuration to engage the wall of the body vessel. The system further can include an occlusion catheter having a proximal end, a distal end, and an occlusion lumen extending longitudinally therein. The occlusion catheter can be disposed within the thrombectomy lumen of the thrombectomy catheter. A second occlusion member can be disposed at the distal end of the occlusion catheter. The second occlusion member can be moveable between a non-expanded configuration and an expanded configuration to engage the wall of the body vessel. The system further can include an aspiration catheter having a proximal end, a distal end, and an aspiration lumen extending longitudinally therein. The aspiration catheter can be disposed within the thrombectomy lumen of the thrombectomy catheter. An articulable nozzle can be disposed at the distal end of the aspiration catheter. The second occlusion member of the occlusion catheter can be extendable distally away from the first occlusion device by a distance such that, when the first and second occlusion members are expanded to engage the wall of the body vessel, a section of the body vessel can be isolated. The articulable nozzle of the aspiration catheter can extend beyond an end opening of the thrombectomy catheter to aspirate thrombus material from the isolated region of the body vessel.

In another example, a method of removing a thrombus accumulation from a body vessel is provided herein. A thrombectomy catheter and an occlusion catheter can be introduced into the body vessel. A first occlusion member of the thrombectomy catheter can be expanded from a non-expanded configuration to an expanded configuration to engage a wall of the body vessel. A second occlusion member of the occlusion catheter can be positioned distal to the first occlusion member of the thrombectomy catheter. The second occlusion member can be expanded from the non-expanded configuration to the expanded configuration to engage the wall of the body vessel. A region of the body vessel extending between the first and second occlusion members may be isolated thereby. An aspiration catheter can be introduced into the body vessel. At least one articulable nozzle of the aspiration catheter can be positioned within the isolated region of the body vessel. The articulable nozzle can be extended to a position between the first and second occlusion members and proximate a thrombus accumulation. The thrombus accumulation can be aspirated through the aspiration catheter to remove the thrombus accumulation from the body vessel.

BRIEF DESCRIPTIONS OF THE DRAWINGS

FIG. 1a is a perspective view of one example of a thrombectomy system.

FIG. 1b is a perspective view of one example of an articulable nozzle.

FIG. 1c is a cross-sectional view of the thrombectomy system illustrated in FIG. 1a.

FIG. 2 is a perspective view of another example of a thrombectomy system.

FIG. 3 is a perspective view of another example of an aspiration catheter having multiple articulable nozzles.

FIGS. 4a-4h illustrate a method of aspirating an isolated region of a body vessel.

DETAILED DESCRIPTION OF THE DRAWINGS AND THE PRESENTLY PREFERRED EMBODIMENTS

Figure 4A:
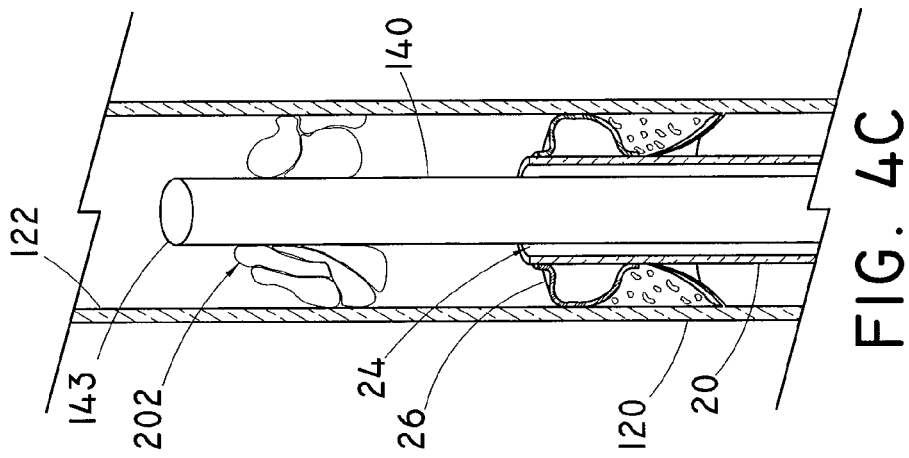

For the purposes of promoting an understanding of the principles of the present disclosure, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates. In the following discussion, the terms "proximal" and "distal" will be used to describe the opposing axial ends of the system, as well as the axial ends of various component features. The "proximal" end refers to the end of the system (or component thereof) that is closest to the operator during use of the system. The "distal" end refers to the end of the system (or component thereof) that is initially inserted into the patient, or that is closest to the patient. The term "catheter" shall have its plain and ordinary meaning, rather than any lexicographic definition. Given the configuration of a vessel passageway or the channel of an endoscope or accessory device, a variety of catheters of different shapes and sizes can be used depending on the particular medical applications for the catheter. The term "tubular" includes any tube-like, cylindrical, elongated, shaft-like, rounded, oblong, or other elongated longitudinal shaft.

Generally speaking, the present disclosure is directed to a thrombectomy system. The system may be used for removing any sort of material that may be partially or completely occluding a body vessel. Such occlusions may be caused by, for example, emboli, plaque, or thrombi. The system may be particularly useful for aspirating thrombus material from an isolated portion of a blood vessel such as an artery or a vein. Such an isolated portion of a blood vessel may include a valve member, such as a coronary or venous valve. In one example, the system may be useful for removing thrombus accumulation disposed in a space between such a valve member and an interior wall of the body vessel. Other applications for the system will become readily apparent to one skilled in the art from the detailed description.

FIGS. 1a-1c depict one embodiment of a thrombectomy system 10 having a thrombectomy catheter 20, an occlusion catheter 40, and an aspiration catheter 60. The thrombectomy catheter 20 can include a generally tubular body 21 having a proximal end and a distal end 23. The proximal end of the thrombectomy catheter 20 may include a handle having an adapter configured to receive the occlusion catheter and/or the aspiration catheter as further described herein. The occlusion catheter and/or the aspiration catheter may be received within a common adapter or within multiple adapters. An additional adapter (e.g., a Luer lock adapter) may be included to engage a device for applying negative pressure as further described herein. The proximal end of the thrombectomy catheter 20 may be configured as a catheter hub such as that described in U.S. Pat. No. 7,713,260 to Lessard et al., which is incorporated by reference herein in its entirety.

The tip of the distal end 23 may have a planar, flat, rounded, chamfered, distally tapered, or arrow-head shape, or may be otherwise atraumatically shaped, to minimize trauma to the body vessel and/or pain and discomfort during introduction and/or navigation of the thrombectomy catheter 20 within the body of the patient. A thrombectomy lumen 24 can extend longitudinally within the thrombectomy catheter 20 between the proximal end and the distal end 23. The thrombectomy lumen 24 can be in communication with an end opening 25 at the distal end 23 of the thrombectomy catheter 20. The end opening 25 can allow access to an isolated portion of a body vessel as further described herein. The thrombectomy catheter 20 can have a size and shape suitable for insertion and placement within a body vessel such as an artery or a vein. For example, the thrombectomy catheter 20 may have an outer diameter of from about 9 to about 15 French (Fr) and a length of from about 70 to about 110 centimeters (cm).

The thrombectomy catheter 20 further can include a first occlusion member 26 disposed about a portion of the distal end 23 thereof. The first occlusion member 26 can surround an outer circumference of the body 21 of the thrombectomy catheter 20. The body 21 of the thrombectomy catheter 20 can extend at least to a distal end of the first occlusion member 26 such that the end opening 25 can be disposed in a position distal of the first occlusion member 26. Optionally, the body 21 may extend further distally beyond the first occlusion member 26 as shown in FIG. 1a. This arrangement can permit the thrombectomy lumen 24 to extend distally beyond the first occlusion member 26 to provide access to the isolated portion of the body vessel through the end opening 25. The first occlusion member 26 can be moveable between a non-expanded configuration and an expanded configuration to sealably engage an inner wall 101 of a body vessel 100. In the expanded configuration, the first occlusion member 26 preferably can fill an entire space between the thrombectomy catheter 20 and the inner wall 101 of the body vessel 100 to substantially inhibit any fluid from flowing within the body vessel. In other words, the first occlusion member 26 and the thrombectomy catheter 20 may substantially fill an entire cross section of the body vessel 100. The first occlusion member 26 can be any type of occlusion and/or embolization device known in the art.

The body 21 of the thrombectomy catheter 20 can be formed from any appropriate material known in the art. Preferably, the body 21 can be formed from a conventional pliable radiopaque plastic. Non-limiting examples of suitable materials include polytetrafluoroethylene (PTFE), polyurethane, fluoroplastic, polyester, nylon, polypropylene, and silicone plastic. Additionally, the first occlusion member 26 can be made of any appropriate flexible material known in the art. Non-limiting examples of such a material include nylon, polyester, polyurethane, PTFE, latex, rubber, silicone plastic, and mixtures thereof. The first occlusion device can be attached to the body 21 of the thrombectomy catheter 20 by any suitable means known in the art, such as for example, hot melt bonding, adhesive bonding, solvent bonding, or ultrasonic welding. In one example, the first occlusion member 26 can be an expandable support structure covered by an impermeable membrane. In another example, the first occlusion member 26 can be an inflatable balloon as shown in FIG. 1a. One example of a suitable inflatable balloon is described in U.S. Pat. App. Pub. No. 2010/0036314 to Burton et al., incorporated by reference herein in its entirety. To that end, the thrombectomy catheter 20 further can include an inflation tube (not shown) extending longitudinally along a length of the thrombectomy catheter between the proximal end and the distal end 23. The inflation tube can have an inflation lumen extending longitudinally therein and being in fluid communication with an interior volume of the inflatable balloon. The inflation tube may be disposed along the interior of the body 21 of the thrombectomy catheter 20 within the thrombectomy lumen 24. Alternatively, the inflation tube may be disposed along the exterior of the body 21 in abutting contact with an outer surface of the body of the thrombectomy catheter 20. The inflatable balloon can be inflated and/or deflated by supplying and/or withdrawing an inflation fluid through the inflation lumen at the proximal end of the thrombectomy catheter as is well known in the art. One example of a suitable balloon inflation lumen configuration is described in U.S. Pat. No. 7,578,295 to Kurrus, incorporated by reference herein in its entirety.

The occlusion catheter 40 can include a generally tubular body 41 having a proximal end and a distal end 43. The tip of the distal end 43 may have a planar, flat, rounded, chamfered, distally tapered, or arrow-head shape, or may be otherwise atraumatically shaped to minimize trauma to the body vessel and/or pain and discomfort during introduction and/or navigation of the occlusion catheter 40 within the body of the patient. The body 41 of the occlusion catheter 40 can be formed from any suitable material known in the art as described in reference to the thrombectomy catheter 20. The body 41 of the occlusion catheter 40 can be formed from the same or a different material than that used to form the body 21 of the thrombectomy catheter 20. An occlusion lumen 44 can extend longitudinally within the occlusion catheter 40 between the proximal end and the distal end 43. The occlusion catheter 40 can have a size and shape suitable for insertion and placement within a body vessel such as an artery or vein. More specifically, the occlusion catheter 40 can have a size and shape suitable for insertion through the thrombectomy lumen 24 of the thrombectomy catheter 20 as further described herein. For example, the occlusion catheter 40 may have an outer diameter of from about 5 to about 7 Fr and a length of from about 70 to about 110 cm.

The occlusion catheter 40 further can include a second occlusion member 45 disposed at the distal end 43 thereof. The second occlusion member 45 can be moveable between a non-expanded configuration and an expanded configuration to contact the inner wall 101 of the body vessel 100. In the expanded configuration, the second occlusion member 45 of the occlusion catheter 40 preferably can fill an entire cross section of the body vessel 100 to substantially inhibit any fluid from flowing within the body vessel. The second occlusion member 45 can be any type of occlusion and/or embolization device known in the art. For example, the second occlusion member 45 can be an inflatable balloon as shown in FIG. 1a. To that end, the occlusion catheter 40 can include an inflation lumen (not shown) extending longitudinally along a length of the occlusion catheter 40 between the proximal end and the distal end 43. The occlusion lumen 44 may serve as the inflation lumen. Alternatively, the inflation lumen may extend longitudinally within an inflation tube (not shown) that can be disposed along the interior or exterior of the body of the occlusion catheter. The inflation lumen can be in fluid communication with an interior volume of the inflatable balloon. The second occlusion member 45 can be inflated and/or deflated by supplying and/or withdrawing an inflation fluid through the inflation lumen at the proximal end of the occlusion catheter as is well known in the art and described herein with respect to the first occlusion member 26. The second occlusion member 45 can be formed from any appropriate flexible material known in the art as described herein. The second occlusion member 45 may be formed from the same or a different material than that used to form the first occlusion member 26. The second occlusion member 45 can be attached to the body 41 of the occlusion catheter 40 by any suitable means known in the art as described herein.

The occlusion catheter 40 can be slidably received within the thrombectomy lumen 24 of the thrombectomy catheter 20. The thrombectomy catheter 20 and the occlusion catheter 40 may be coaxial. The distal end 43 of the occlusion catheter 40 can be extendable through the end opening 25 and distally away from the distal end 23 of the thrombectomy catheter 20 by a distance A. The distance A can be dimensioned such that a region 102 of the body vessel 100 can be isolated by expanding the first and second occlusion members 26, 45 to the expanded configuration as further described herein. Fluid flow through the body vessel 100 may be substantially inhibited when either of the first and second occlusion members 26, 45 is in the expanded configuration. When both the first and second occlusion members 26, 45 are in the expanded configuration, fluid communication between the isolated region 102 and other portions of the body vessel 100, either upstream or downstream of the isolated region, may be substantially inhibited.

The aspiration catheter 60 can include a generally tubular body 61 having a proximal end and a distal end 63. The body 61 of the aspiration catheter 60 can be made of any suitable material known in the art as described herein with respect to the thrombectomy catheter 20. An aspiration lumen 64 can extend longitudinally within the aspiration catheter 60 between the proximal end and the distal end 63. The aspiration catheter 60 can have a size and shape suitable for insertion and placement within a body vessel such as an artery or a vein. More specifically, the aspiration catheter 60 can have a size and shape suitable for insertion through the thrombectomy lumen 24 of the thrombectomy catheter 20 and/or the occlusion lumen 44 of the occlusion catheter 40 as further described herein. For example, the aspiration catheter 60 may have an outer diameter of from about 5 to about 7 Fr and a length of from about 70 to about 110 cm.

The aspiration catheter 60 further can include at least one articulable nozzle 65 disposed at the distal end 63 thereof. The articulable nozzle 65 can be capable of articulating as further described herein. In other words, the articulable nozzle 65 can be movable by, for example, rotation, bending, and/or translational displacements along any three dimensional direction. For instance, such articulation may be axial, longitudinal, forward, backward, orthogonal, lateral, transverse, rotational, pivotable, sloping incline or decline, swinging, torsional, revolving, and/or other forms of translation and/or rotation relative to a coordinate system. A first coordinate system is shown in FIG. 1c where the z-axis is the longitudinal axis of the thrombectomy catheter 20, and the x-axis and the y-axis are substantially perpendicular to the z-axis and to each other. A second coordinate system parallel to the first coordinate system is shown in FIG. 1c where the c-axis is the longitudinal axis of the aspiration catheter 60, and the a-axis and the b-axis are substantially perpendicular to the c-axis and to each other. Arrows illustrate that the aspiration catheter can be rotated about the c-axis, as well as moved longitudinally along the c-axis, and in any direction along the x-axis and/or the y-axis within the annular space defined between the thrombectomy catheter 20 and the occlusion catheter 40.

The articulable nozzle 65 can be formed from any suitable material known in the art. Preferably, such a material can be strong yet sufficiently flexible and resilient to allow articulation of the articulable nozzle 65 as described herein. Non-limiting examples of such materials include elastomeric materials such as latex, silicone, urethane, thermoplastic elastomer, nickel titanium alloy, polyether etherketone (PEEK), polyimide, polyurethane, cellulose acetate, cellulose nitrate, polyethylene terephthalate (PET), polyamide, polyester, polyorthoester, polyanhydride, polyether sulfone, polycarbonate, polypropylene, high molecular weight polyethylene, PTFE, or mixtures or copolymers thereof, polylactic acid, polyglycolic acid or copolymers thereof, polycaprolactone, polyhydroxyalkanoate, polyhydroxy-butyrate valerate, polyhydroxy-butyrate valerate, or another polymer or suitable material. Optionally, the articulable nozzle 65 may be formed from an anisotropic material that can be relatively compliant in an axial direction as compared to a transverse direction as opposed to an isotropic material that can be relatively uniformly compliant independent of direction.

The articulable nozzle 65 can include a nozzle lumen 66 and an end opening 67. The nozzle lumen 66 can be in communication with the aspiration lumen 64 of the aspiration catheter 60. The articulable nozzle 65 can be moveable between a neutral configuration and any number of bending configurations (one such bending configuration shown in phantom lines) as shown in FIG. 1b. There may be a number of bending configurations along a continuum from the neutral configuration to a maximum articulation allowable by the articulable nozzle 65. In the neutral configuration, the articulable nozzle 65 can be substantially coaxial with the aspiration catheter 60 such that the end opening 67 of the articulable nozzle can be disposed along the longitudinal c-axis of the aspiration catheter and can face in a distal direction with respect to the body 61 of the aspiration catheter. In a bending configuration, the articulable nozzle 65 can be deflected such that the end opening 67 of the articulable nozzle can be disposed adjacent to the longitudinal c-axis of the aspiration catheter 60 and can face in a direction other than distally with respect to the body 61 of the aspiration catheter.

The aspiration catheter 60 further can include a means for manipulating the articulable nozzle 65. One example of a suitable means for manipulating the articulable nozzle 65 can include a control wire 72 as shown in FIG. 1b. The control wire 72 can extend longitudinally along a length of the aspiration catheter 60 and the articulable nozzle 65 between the proximal end of the aspiration catheter and the end of the articulable nozzle. The control wire 72 can be slidably received within the aspiration lumen 64 of the aspiration catheter 60. Alternatively, the control wire 72 can be slidably received within a control wire lumen 73 of a control wire tube 74. The control wire tube 74 can be disposed along the interior of the aspiration catheter 60. Alternatively, the control wire tube 74 can be disposed along the exterior and adjacent to the aspiration catheter 60 such that the control wire tube is in abutting contact with an exterior surface of the aspiration catheter. The control wire 72 can be fixedly attached to at least a portion (e.g., the distal end) of the articulable nozzle 65 proximate the end opening 67. A control wire sleeve 75 can extend along a portion of the articulable nozzle 65. The control wire 72 can be slidably received within a lumen 76 of the control wire sleeve 75. The control wire sleeve may be configured to lengthen and shorten with the articulable nozzle 65 during articulation as further described herein. The control wire 72 can be a flexible wire made of any suitable material known in the art. Non-limiting examples of such material include biocompatible metal such as stainless steel (e.g., 316 L SS), titanium, tantalum, and nitinol; and high-strength polymer. With the articulable nozzle 65 in the neutral configuration, advancing the control wire 72 proximally with respect to the aspiration catheter 60 can cause a longitudinal segment of the articulable nozzle abutting or proximate to the control wire to elongate longitudinally in a lengthwise direction. Such selective elongation of the longitudinal segment can cause the articulable nozzle 65 to articulate toward a bending configuration (as shown in phantom lines in FIG. 1b). Conversely, retracting the control wire 72 distally can cause the longitudinal segment to shorten longitudinally in a lengthwise direction, thereby causing the articulable nozzle 65 to articulate back toward the neutral configuration.

Another example of a suitable means for manipulating the articulable nozzle 65 can include at least one control channel (not shown). The control channel can extend longitudinally along a length of the aspiration catheter 60 and the articulable nozzle 65 between the proximal end of the aspiration catheter and the distal end of the articulable nozzle. Preferably, the control channel can be disposed within, or formed within, outer walls of the body 61 of the aspiration catheter 60 and a body of the articulable nozzle 65. Alternatively, the control channel lumen can extend longitudinally within a distinct control channel tube. The control channel can be configured to elongate longitudinally in a lengthwise direction in response to an increased pressure applied to the control channel. Such elongation can cause a longitudinal segment of the articulable nozzle 65 abutting or proximate to the control channel to elongate longitudinally in a lengthwise direction. Such selective elongation of the longitudinal segment can cause the articulable nozzle 65 to articulate toward a bending configuration. Conversely, the control channel can be configured to shorten longitudinally in a lengthwise direction in response to a decreased pressure applied to the control channel. Such shortening can cause the longitudinal segment to shorten longitudinally in a lengthwise direction, thereby causing the articulable nozzle 65 to articulate back toward the neutral configuration. One example of a suitable means for manipulating the articulable nozzle 65 is described in U.S. Pat. No. 7,608,056 to Kennedy, II, which is incorporated by reference herein in its entirety.

In FIG. 1a, the aspiration catheter 60 can be slidably received within the thrombectomy lumen 24 of the thrombectomy catheter 20. The aspiration catheter 60 can be disposed adjacent to the occlusion catheter 40 within the thrombectomy lumen 24 of the thrombectomy catheter 20 in a side-by-side configuration. The distal end 63 of the aspiration catheter 60 can be extendable through the end opening 25 and distally away from the distal end 23 of the thrombectomy catheter 20 to be positioned for aspiration of thrombus or other occlusive material from the isolated region 102 of the body vessel 100 as further described herein. Additionally, the aspiration catheter 60 can be free to move within the thrombectomy lumen 24 of the thrombectomy catheter 20 in the annular space between the occlusion catheter 40 and the thrombectomy catheter 20, as shown in FIG. 1*c*, for more efficient access to various portions of the isolated region 102 of the body vessel 100. For example, the aspiration catheter 60 can be free to translate axially in the annular space between the occlusion catheter 40 and the thrombectomy catheter 20 up to 360 degrees around the occlusion catheter, translated longitudinally in proximal and/or distal directions, and/or rotated about a longitudinal axis of the aspiration catheter. Additionally, the articulable nozzle 65 can be articulated as described herein to reach any portion of the isolated region 102 of the body vessel 100.

One of ordinary skill in the art will appreciate that the dimensions of the various components described herein will depend on various factors. These factors include the intended use of the system and the body vessel into which the components of the system may be positioned. In general, however, each of the thrombectomy catheter 20, the occlusion catheter 40, and the aspiration catheter 60 can be elongate, meaning that the catheter can be relatively long enough to reach a target site at a region within the body of the patient. The overall length of each catheter may vary greatly, however, depending on the intended medical procedure to be performed and/or the location of the target site within the body of the patient.

Generally, each catheter may be made by any method known in the art such as extrusion, pultrusion, injection molding, transfer molding, flow encapsulation, fiber winding on a mandrel, or lay-up with vacuum bagging. A variety of suitable materials may be used, so long as each catheter or a portion thereof is sufficiently flexible for the intended purpose. For example, suitable materials include surgical stainless steel or biologically compatible metals, polymers, plastics, alloys (including super-elastic alloys), or composite materials that are either biocompatible or capable of being made biocompatible. Flexible sections of the catheters may be made of any suitable material (natural, synthetic, plastic, rubber, metal, or combination thereof) that is strong yet flexible and resilient.

For portions of each of the catheters that may contact the patient, the material of construction may need to be biocompatible or capable of being made biocompatible, such as by coating, chemical treatment, or the like. Optionally, a thin PTFE heat shrinkable material may coat the catheter. The heat shrinkable nature of these materials may facilitate manufacturing and may provide a lubricious coating to facilitate navigation of the catheter within the body of the patient. The thickness of the coating may vary between about 0.01 mm and about 0.20 mm. In another embodiment, the coating thickness may vary between about 0.01 mm and about 0.05 mm. In yet another embodiment, the coating thickness my vary between about 0.01 mm and about 0.02 mm. These thicknesses may provide suitable coatings while not adding significantly to the overall thickness of the catheter. The coating may be applied to substantially all or a portion of the length of the catheter. With or without PTFE coating, the catheter or an insertion portion thereof may be treated with a hydrophilic coating or hybrid polymer mixture. Such materials may include any suitable polyvinyl puroladine and cellulose esters in organic solvent solutions. These solutions may make the catheter surface particularly lubricious when in contact with body fluids, which may aid in navigation.

Radiopaque materials and markers such as bismuth or gold may be added to the coating. Also, various portions of each of the catheters (e.g., the distal ends 23, 43 and/or the distal end of the articulable nozzle 65) may include radiopaque materials and markers. Several examples of suitable radiopaque materials and markers are known in the art, and any suitable material and/or marker can be used with the various embodiments of this disclosure.

FIG. 2 depicts another embodiment of the thrombectomy system 110. The occlusion catheter 140 further can include at least one nozzle port 146 formed in the body 141 at the distal end 143 thereof. The aspiration catheter 60 further can be slidably received within the occlusion lumen 144 of the occlusion catheter 140. The thrombectomy catheter 20, occlusion catheter 140, and aspiration catheter 60 may be in a coaxial relationship that may form a smaller delivery profile. The articulable nozzle 65 of the aspiration catheter 60 can be extendable through the nozzle port 146 of the occlusion catheter 140 to aspirate thrombus material from the isolated region 102 of the body vessel 100 as further described herein. The embodiment of FIG. 2 may assist a clinician in navigating the distal ends of the occlusion and aspiration catheters to the desired position. For example, the occlusion catheter may be navigated through a valve member 121 as shown in FIG. 2. Once the leaflets of the valve member 121 have been pushed aside by the occlusion catheter, the aspiration catheter may be positioned distally of the valve member without further disturbing the leaflets of the valve member. Such an embodiment also may allow the occlusion catheter and the aspiration catheter to be navigated through the body vessel together, e.g., with the aspiration catheter disposed within the occlusion catheter, to save time during a thrombectomy procedure.

FIG. 3 depicts another embodiment of the aspiration catheter 260 that can include a plurality of tubular bodies. In one example, the aspiration catheter 260 can include a first generally tubular body 261*a* and a second generally tubular body 261*b*; however, more than two tubular bodies such as three, four, or more are further contemplated. Each of the first and second bodies 261*a*, 261*b* can have a proximal end and a distal end 263*a*, 263*b*, respectively. The bodies 261*a*, 261*b* can be disposed adjacent to one another in a side-by-side configuration such that each one of the bodies can be in abutting contact with the other at an outer surface of the body. Each of the bodies 261*a*, 261*b* can be joined to the other along at least a portion of the outer surface of the body. Additionally, each of the bodies 261*a*, 261*b* may be joined to the other along substantially an entire length of the body between the proximal end and the distal end of the body. The first aspiration lumen 264*a* can extend longitudinally within the body 261*a*. Likewise, the second aspiration lumen 264*b* can extend longitudinally within the body 261*b*. Alternatively, the aspiration catheter 260 may include a single tubular body, e.g., the body 61 as shown in FIG. 1*a*, having the second aspiration lumen 264*b* disposed adjacent to the first aspiration lumen 264*a* within the single body of the aspiration catheter.

In FIG. 3, the aspiration catheter 260 can include a first articulable nozzle 265*a* and a second articulable nozzle 265*b*. A first nozzle lumen 266*a* of the first articulable nozzle 265*a* can be in communication with the first aspiration lumen 264*a* of the aspiration catheter 260. The first nozzle lumen 266*a* may terminate in an end opening 267*a*. Similarly, a second nozzle lumen 266*b* of the second articulable nozzle 265*b* can be in communication with the second aspiration lumen 264*b* and may terminate in an end opening 267*b*. The aspiration lumens 264*a*, 264*b* may be in communication with one another such that a negative pressure may be applied, as further described herein, to both lumens simultaneously from a common source. Alternatively, the aspiration lumens 264a, 264b may not be in communication with one another such that the same or different negative pressures may be applied separately to each of the aspiration lumens. The aspiration catheter 260 further can include a first means for manipulating the articulable nozzle 265a and a second means for manipulating the articulable nozzle 265b. The first and second articulable nozzles 265a, 265b may be manipulated and/or articulated, as described herein, to aspirate the isolated region 102 of the body vessel 100.

Although the system has been described in connection with its primary intended use for removing thrombus material from an isolated region of a body vessel, those skilled in the art will appreciate that the system may also be used in other applications where accurately controllable aspiration of a specific location within the body may be desirable.

FIGS. 4a-4h illustrate a method of removing thrombus material from an isolated region of a body vessel. The method can be used, for example, to aspirate thrombus material that can be partly or completely occluding a body vessel such as a vein and/or thrombus accumulation that can be disposed in an area between a body vessel valve or structure, such as a venous valve and a vein wall. Although reference will be specifically made to a vein and a venous valve, it can be appreciated that the method can be used for other vessels and vessel structures. Although the method will be described with reference to the embodiment illustrated in FIG. 2, it can be appreciated that the method may be practiced using other embodiments described herein and/or variations thereof.

Figure 4B:
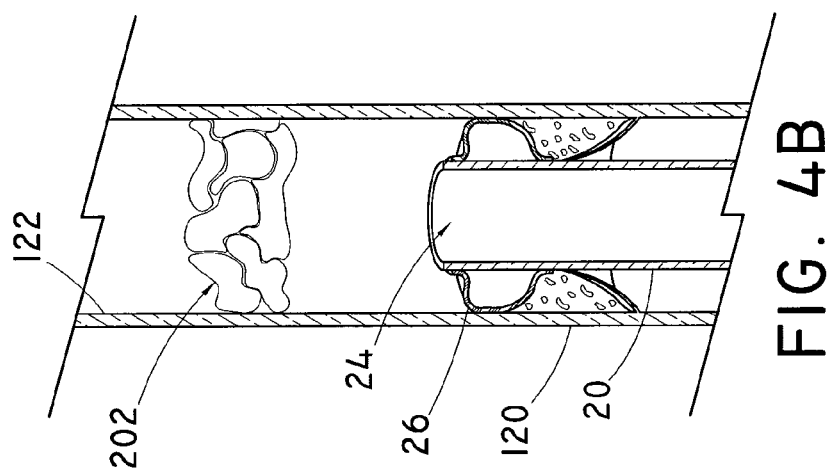

In FIG. 4a, the distal end 23 of the thrombectomy catheter 20 can be inserted percutaneously into a vein 120. Optionally, a dilator and/or introducer (not shown) may be used to aid in inserting the thrombectomy catheter as is well known in the art. The distal end 23 of the thrombectomy catheter 20 can be translated distally through the vein 120 to position the distal end proximate to and distal of a venous valve 121 and proximal of a thrombus material 202. Optionally, a guide wire (not shown) may be used to aid in advancing and/or positioning the thrombectomy catheter within the vein as is well known in the art. In FIG. 4b, the first occlusion member 26 can be expanded from the non-expanded configuration to the expanded configuration to sealably engage a wall 122 of the vein 120. Expansion of the first occlusion member 26 may occlude the vein 120 to substantially inhibit fluid flow therethrough, and preferably the passage of thrombus debris proximal of the first occlusion member.

Figure 4C:
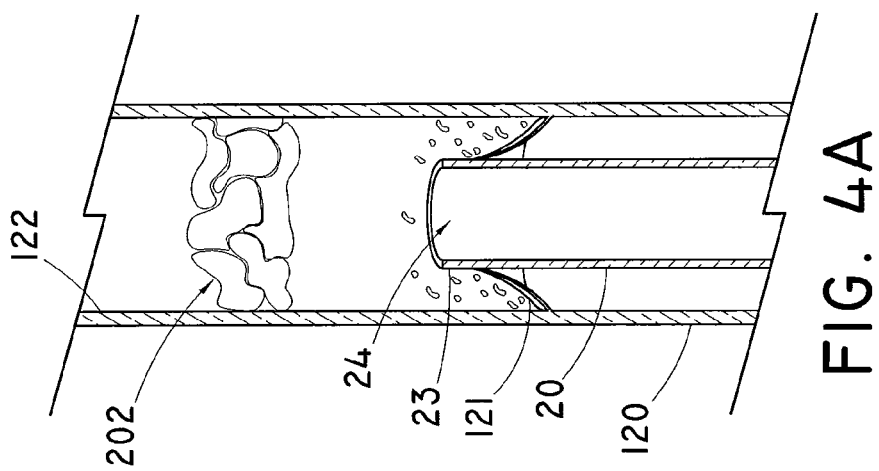

In FIG. 4c, the occlusion catheter 140 can be inserted into the thrombectomy lumen 24 of the thrombectomy catheter 20. Optionally, the occlusion catheter 140 may be inserted into the thrombectomy lumen 24 of the thrombectomy catheter 20 prior to insertion of the thrombectomy catheter into the body of the patient. Such a procedure may eliminate the need to insert the thrombectomy and occlusion catheters separately into the body of the patient to reduce the amount of time required to complete the method according to this disclosure. The occlusion catheter 140 can be advanced distally through the thrombectomy catheter 20 and the vein 120 to position the distal end 143 of the occlusion catheter 140 proximate to and distal of the thrombus material 202.

In FIG. 4d, the distal tip of the occlusion catheter 140 may pierce through the thrombus material 202 to reach a position distal of the thrombus material. It is contemplated that the distal tip of the occlusion catheter may be configured for piercing the thrombus material. To this end, the distal tip of the occlusion catheter can have a beveled or pointed tip. Alternatively, the distal tip of the occlusion catheter 140 may pass through a space between the thrombus material 202 and the wall 122 of the vein 120 to reach the position distal of the thrombus material. The second occlusion member 145 can be expanded from the non-expanded configuration to the expanded configuration to engage the wall 122 of the vein 120. Expansion of the second occlusion member 145 may occlude the vein 120 to substantially inhibit fluid flow therethrough, and preferably the passage of thrombus debris distal of the second occlusion member. Accordingly, a first region 123 of the vein 120 can be isolated between the first occlusion member 26 and the second occlusion member 145. In this manner, blood, thrombus material, and/or other fluid or debris can be prevented from migrating into and/or outside of the first isolated region 123 of the vein 120. Particularly, any debris that may be generated by piercing the thrombus material 202 with the distal tip of the occlusion catheter 140 can be contained within the isolated region 123 of the vein 120. Negative pressure can be applied to the thrombectomy lumen 24 at the proximal end of the thrombectomy catheter 20 to create a suction pressure at the end opening 25 thereof for removal of the thrombus material 202 and/or other debris. Such negative pressure may be applied by any means known in the art. For example, negative pressure may be applied using a syringe. The syringe may be coupled to an adapter (e.g., a Luer lock fitting) at the proximal end of the thrombectomy catheter. Negative pressure may be applied by retracting a plunger of the syringe to draw fluid, thrombus material, and/or debris through the thrombectomy lumen of the thrombectomy catheter and into a tube of the syringe. Negative pressure also may be applied using a suction device employing, for example, a bulb and tube arrangement, a hand pump, and/or a diaphragm pump. Other suction devices will be apparent to those having ordinary skill in the art.

In FIG. 4e, after the initial removal of the thrombus material and/or debris with the thrombectomy catheter 20, the occlusion catheter 140 may be moved relative to the distal end 23 of the thrombectomy catheter 20, such as by retraction of the second occlusion member 145 proximally toward the distal end 23 of the thrombectomy catheter. The thrombus material 202 can be urged proximally by such proximal movement of the second occlusion member 145. Additionally, the thrombus material 202 can be urged into the end opening 25 of the thrombectomy catheter 20 by the suction created therein. Accordingly, the thrombus material 202 and/or debris can be aspirated and removed from the vein 120 through the thrombectomy lumen 24 of the thrombectomy catheter 20.

The first occlusion member 26 can be moved from the expanded configuration to the non-expanded configuration to disengage from the wall 122 of the vein 120 as shown in FIG. 4f. In FIG. 4g, the thrombectomy catheter 20 may be moved relative to the occlusion catheter 140, such as by retraction of the thrombectomy catheter to position the distal end 23 proximate to and proximal of the venous valve 121. The first occlusion member 26 can be moved from the non-expanded configuration to the expanded configuration to sealably engage the wall 122 of the vein 120 to isolate a second region 124. The venous valve 121 may be disposed within the second isolated region between the first occlusion member and the second occlusion member. The second isolated region 124 may extend proximal of and substantially overlap with the first region 123.

Figure 4H:
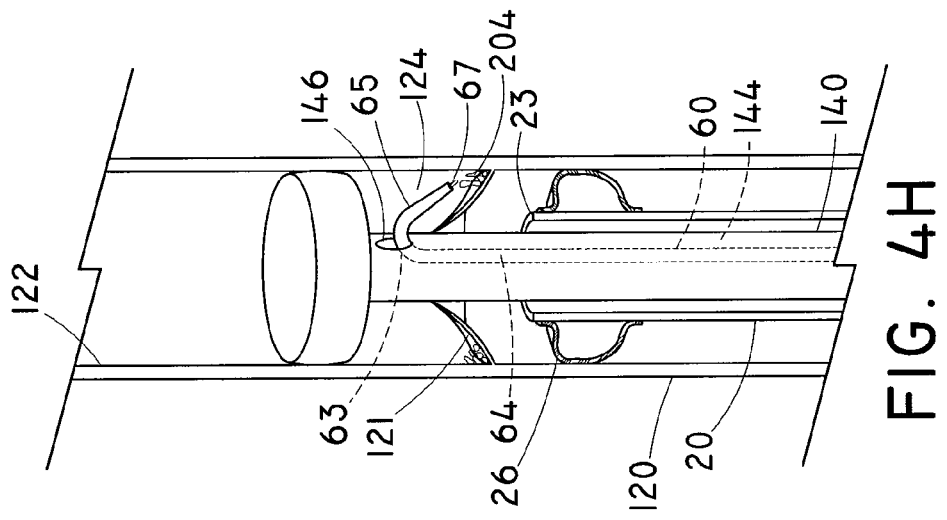
Figure 4G:
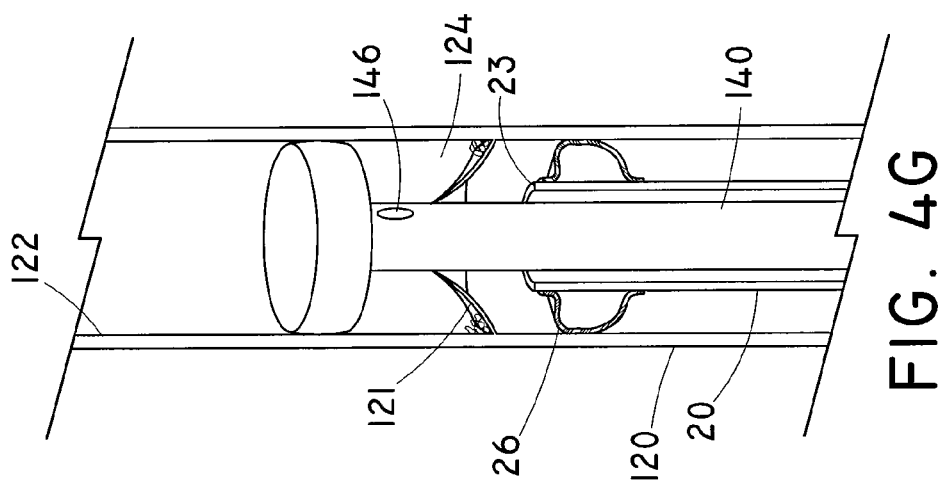

In FIG. 4h, the aspiration catheter 60 can be inserted into the occlusion lumen 144 of the occlusion catheter 140. The aspiration catheter 60 can be advanced distally through the occlusion catheter 140, the thrombectomy catheter 20, and the vein 120 to position the distal end 63 of the aspiration catheter adjacent to the nozzle port 146 of the occlusion catheter 140. The articulable nozzle 65 can be manipulated as described herein to extend through the nozzle port 146 and into the second isolated region 124. The articulable nozzle 65 can be manipulated and/or the aspiration catheter 60 can be translated and/or rotated as described herein to position the end opening 67 of the articulable nozzle 65 proximate to a thrombus accumulation 204 disposed in a space between the venous valve 121 and the wall 122 of the vein 120. The position of the aspiration catheter 60 within the occlusion catheter 140 can be adjusted and/or the means for manipulating the articulable nozzle 65 can be operated to position the end opening 67 of the aspiration catheter 60 as desired. Negative pressure can be applied to the aspiration lumen 64 of the aspiration catheter 60 to create a suction pressure at the end opening 67 thereof. Such negative pressure may be applied by any means known in the art as described with respect to the thrombectomy catheter. A device for applying negative pressure may be coupled to an adapter (e.g., a Luer lock fitting) at the proximal end of the aspiration catheter. The same device may be used to apply negative pressure to the thrombectomy catheter and the aspiration catheter. Alternatively, different devices may be used. The thrombus accumulation 204 can be urged into the end opening 67 of the aspiration catheter 60 by the suction pressure created therein. Accordingly, the thrombus accumulation 204 can be aspirated and removed from the vein 120.

It can be appreciated by those skilled in the art that specific features of each embodiment of the system and/or method are interchangeable among the various embodiments, even where no references to the specific features are made.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments, and may be combined with each other and/or with currently-known or future-developed technologies while remaining within the scope of the claims presented here. It is therefore intended that the foregoing detailed description be regarded as illustrative rather than limiting. And it should be understood that the following claims, including all equivalents, are intended to define the spirit and scope of this invention.

I claim:

1. A method for removing a thrombus accumulation from a space between a venous valve and a wall of a vein, the valve comprising a leaflet opening from a first side of the vein to a second side of the vein, the thrombus accumulation being disposed along the second side of the vein in the space between the venous valve and the wall of the vein, the method comprising:

introducing an occlusion catheter within the vein;

positioning a first occlusion member of the occlusion catheter on the second side of the vein;

expanding the first occlusion member of the occlusion catheter to an expanded configuration to engage the wall of the vein;

introducing an aspiration catheter within the vein and through said valve from the first side to the second side of the vein, the aspiration catheter comprising an aspiration lumen and an articulable nozzle with a nozzle lumen and an end opening;

positioning the end opening of the articulable nozzle on the second side of the vein proximate the thrombus accumulation, the nozzle comprising a bent configuration with the nozzle lumen being acutely angled relative to said aspiration lumen and said end opening facing away from a distal direction of said aspiration catheter; and aspirating the thrombus accumulation through the end opening, nozzle lumen and aspiration lumen of the aspiration catheter to remove the thrombus accumulation from the space between the valve and the wall of the vein.

2. The method of claim 1, further comprising introducing a thrombectomy catheter within the vein, positioning a second occlusion member of the thrombectomy catheter on the first side of the vein, and expanding the second occlusion member of the thrombectomy catheter to an expanded configuration to engage the wall of the vein, the valve and the thrombus accumulation thereby being isolated between the first and second occlusion members, wherein the nozzle is positioned between the first and second occlusion members to aspirate the thrombus accumulation.

3. The method of claim 2, wherein the first and second occlusion members are inflatable balloons.

4. The method of claim 2, further comprising introducing the occlusion catheter and the aspiration catheter within a thrombectomy lumen of the thrombectomy catheter, extending the first occlusion member of the occlusion catheter beyond a distal end opening of the thrombectomy catheter to expand the first occlusion member on the second side of the vein, and extending the nozzle of the aspiration catheter beyond the distal end opening of the thrombectomy catheter to aspirate the thrombus accumulation.

5. The method of claim 4, wherein the occlusion catheter and the aspiration catheter are adjacent each other side-by-side within the thrombectomy lumen of the thrombectomy catheter.

6. The method of claim 5, wherein the aspiration catheter is configured to move 360 degrees around the occlusion catheter within an annular space defined between the thrombectomy catheter and the occlusion catheter.

7. The method of claim 5, wherein the aspiration catheter comprises at least two nozzles, each nozzle being in communication with a separate aspiration lumen.

8. The method of claim 4, wherein the occlusion catheter further comprises an occlusion lumen extending longitudinally therein and a nozzle side port formed therein, and further comprising introducing the aspiration catheter within the occlusion lumen of the occlusion catheter and extending the nozzle through the nozzle side port to aspirate the thrombus accumulation.

9. The method of claim 8, wherein the aspiration catheter comprises at least two nozzles, each nozzle being extendable through a separate nozzle side port formed in the occlusion catheter.

10. The method of claim 9, wherein the aspiration catheter comprises two nozzles disposed 180 degrees apart from one another.

11. The method of claim 1, wherein the nozzle is articulable between a neutral configuration with the nozzle lumen being substantially coaxial with the aspiration lumen and the bent configuration.

12. The method of claim 11, wherein the nozzle is in the neutral configuration as the aspiration catheter is introduced through the valve and is articulated to the bent configuration after being introduced through the valve.

13. The method of claim 1, further comprising introducing the occlusion catheter through said valve to position the first occlusion member of the occlusion catheter on the second side of the vein.

14. The method of claim 1, wherein a thrombus material at least partially occluding the vein is disposed between the first occlusion member and the valve, further comprising introducing a thrombectomy catheter within the vein and through the valve, and aspirating the thrombus material through a distal end opening of the thrombectomy catheter to remove the thrombus material from the vein.

15. The method of claim 14, wherein the thrombus material is aspirated before the thrombus accumulation is aspirated, and further comprising retracting the thrombectomy catheter through the valve and positioning the distal end opening of the thrombectomy catheter on the first side of the vein before the thrombus accumulation is aspirated.

16. The method of claim 15, further comprising moving the first occlusion member toward the valve and the thrombus accumulation after the thrombus material is aspirated.

17. The method of claim 14, further comprising introducing the occlusion catheter through said valve and piercing the occlusion catheter through said thrombus material to position the first occlusion member of the occlusion catheter on the second side of the vein.

18. The method of claim 1, further comprising introducing a thrombectomy catheter within the vein, positioning a second occlusion member of the thrombectomy catheter on the first side of the vein, and expanding the second occlusion member of the thrombectomy catheter to an expanded configuration to engage the wall of the vein, the valve and the thrombus accumulation thereby being isolated between the first and second occlusion members, wherein the nozzle is positioned between the first and second occlusion members to aspirate the thrombus accumulation, the first and second occlusion members are inflatable balloons, the nozzle is articulable between a neutral configuration with the nozzle lumen being substantially coaxial with the aspiration lumen and the bent configuration, and the nozzle is in the neutral configuration as the aspiration catheter is introduced through the valve and is articulated to the bent configuration after being introduced through the valve.

19. The method of claim 18, further comprising introducing the occlusion catheter through said valve to position the first occlusion member of the occlusion catheter on the second side of the vein, introducing the occlusion catheter and the aspiration catheter within a thrombectomy lumen of the thrombectomy catheter, extending the first occlusion member of the occlusion catheter beyond a distal end opening of the thrombectomy catheter to expand the first occlusion member on the second side of the vein, and extending the nozzle of the aspiration catheter beyond the distal end opening of the thrombectomy catheter to aspirate the thrombus accumulation, wherein the occlusion catheter and the aspiration catheter are adjacent each other side-by-side within the thrombectomy lumen of the thrombectomy catheter.

20. The method of claim 19, wherein a thrombus material at least partially occluding the vein is disposed between the first occlusion member and the valve, further comprising piercing the occlusion catheter through said thrombus material to position the first occlusion member of the occlusion catheter on the second side of the vein, introducing the thrombectomy catheter through the valve, and aspirating the thrombus material through a distal end opening of the thrombectomy catheter to remove the thrombus material from the vein, wherein the thrombus material is aspirated before the thrombus accumulation is aspirated, and further comprising retracting the thrombectomy catheter through the valve and positioning the distal end opening of the thrombectomy catheter on the first side of the vein and moving the first occlusion member toward the valve and the thrombus accumulation after the thrombus material is aspirated and before the thrombus accumulation is aspirated.

* * * * *